United States Patent [19]

Eschenmoser

[11] 3,950,327

[45] Apr. 13, 1976

[54] NITRONES, THEIR MANUFACTURE AND THEIR USE FOR THE MANUFACTURE OF N-SUBSTITUTED ARALIPHATIC ALDEHYDE-NITRONES

[75] Inventor: Albert Eschenmoser, Kusnacht, Switzerland

[73] Assignee: Ciba-Geigy Corporation, Ardsley, N.Y.

[22] Filed: July 24, 1974

[21] Appl. No.: 491,197

Related U.S. Application Data

[63] Continuation-in-part of Ser. No. 398,511, Sept. 18, 1973, Pat. No. 3,894,085.

[30] Foreign Application Priority Data

Sept. 19, 1972 Switzerland..................... 13677/72
Oct. 12, 1972 Switzerland..................... 14962/72

[52] U.S. Cl. .... 260/240 G; 260/326.15; 260/326.4; 260/326.9; 260/346.2 R; 260/347.7; 260/562 R; 260/566 R
[51] Int. Cl.[2]...................................... C07C 119/00
[58] Field of Search....... 260/566 R, 240 G, 326.15, 260/326.4, 326.9, 346.2 R, 347.7, 562 R, 566 R

[56] References Cited
OTHER PUBLICATIONS

Olah, "Friedel–Crafts and Related Reactions" Vol. 1, pp. 28–34 and 201–204 (1963).
Wagner et al., "Synthetic Organic Chemistry" pp. 2–3 (1953).

*Primary Examiner*—Gerald A. Schwartz
*Attorney, Agent, or Firm*—Joseph G. Kolodny; John J. Maitner; Theodore O. Groeger

[57] ABSTRACT

α-Halogen-nitrones of the formula

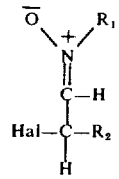

wherein Hal is a bromine or preferably a chlorine atom, $R_1$ represents a cycloalkyl or an alkyl radical and $R_2$ is hydrogen or an organic radical.

Use as intermediates especially for the substitution of a hydrogen atom in aromatic compounds by the radical

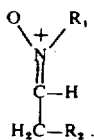

4 Claims, No Drawings

NEW NITRONES, THEIR MANUFACTURE AND THEIR USE FOR THE MANUFACTURE OF N-SUBSTITUTED ARALIPHATIC ALDEHYDE-NITRONES

This is a continuation-in-part of our copending application Ser. No. 398,511, filed Sept. 18, 1973 now U.S. Pat. No. 3,894,085.

The present invention relates to nitrones of the general formula

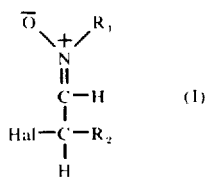

wherein Hal represents bromine atom or preferably a chlorine atom, $R_1$ denotes a cycloalkyl or an alkyl radical and $R_2$ denotes a hydrogen atom or an organic radical.

A cycloalkyl radical is preferably a radical with 5 or 6 ring members, especially the cyclopentyl radical or above all the cyclohexyl radical. An alkyl radical is preferably a lower alkyl radical, very particularly the methyl, ethyl or propyl radical or above all the t-butyl radical. An organic radical is preferably one of the alkyl radicals described above, or a lower alkyl radical substituted by halogen or carbonyl or carboxyl groups, such as the monochloromethyl or dichloromethyl radical, or an aryl radical, above all an unsubstituted or substituted phenyl radical or an aralkyl radical, such as a phenyl-lower alkyl radical, especially a radical of this type wherein the lower alkyl radical contains one, two or three carbon atoms, such as the benzyl, phenyl-1-ethyl, phenyl-2-ethyl or phenyl-propyl radical.

The new compounds are intermediate products which can easily undergo addition reactions with activated or non-activated double bonds and thus serve for the addition and/or substitution of organic radicals at any desired C—C double bonds. They are preferably used for the manufacture of araliphatic N-substituted aldehyde-nitrones which can then be converted in a manner which is in itself known, for example by means of weak acids, into the corresponding araliphatic aldehydes, or be converted by reduction with catalytically activated hydrogen into the corresponding araliphatic amines or be converted by means of metal hydrides to araliphatic hydroxylamines. In other words, they serve in particular for the introduction of an $\alpha$-alkyl-formyl radical into aromatic compounds.

In particular, the $\alpha$-chloro-nitrones of the above formula which in most cases are stable compounds — at low temperatures — can be used for this purpose. However, the $\alpha$-bromo-nitrones can also be used, though they are unstable compounds.

The $\alpha$-chloronitrones of the above formula wherein $R_1$ represents the cyclohexyl radical or the t-butyl radical and $R_2$ denotes hydrogen or a lower alkyl radical have proved particularly suitable for such addition reactions. If $R_2$ is an aryl-propyl radical, an intramolecular reaction can also occur, and in that case the propyl chain forms a 6-membered ring together with the aryl radical.

The new $\alpha$-halogeno-nitrones of the above formula can be obtained when a. a nitrone of the general formula

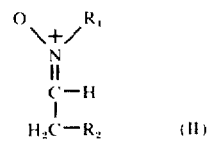

wherein the radicals $R_1$ and $R_2$ have the abovementioned meaning, is halogenated in the $\alpha$-position, or b. a compound of the general formula

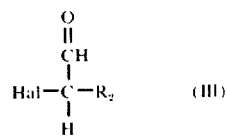

wherein Hal and the radical $R_2$ have the abovementioned meaning, is reacted with a hydroxylamine of the formula

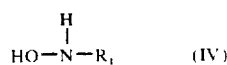

wherein $R_1$ has the abovementioned meaning.

Compounds which release positive halogen, especially chloro- or bromo-amides or -imides, such as chloro- or bromo-acetamide or bromo-propionamide or above all chloro- or bromo-succinimide, are used for the halogenation of the compounds of the formula II. The reaction is carried out in an inert solvent, such as halogenated lower hydrocarbon, for example carbon tetrachloride or trichloromethane, or an ether, such as diethyl ether, or tetrahydrofurane, at a temperature below 50°, especially at 20° to −20°C.

The reaction with the hydroxylamine takes place in the usual manner, again at a low temperature.

A further subject of the invention is the use of the $\alpha$-halogenonitrones obtained according to the invention for the manufacture of N-substituted araliphatic aldehyde-nitrones, that is to say in the reaction of aromatic compounds, especially of aromatic compounds which carry electrophilic substituents, such as alkyl groups or alkoxy groups, for example methyl groups or methoxy groups, or acylamino groups, for example acetylamino groups, with the said nitrone. In this case, substitution by the radical of the general formula

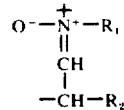

wherein $R_1$ and $R_2$ have the abovementioned meaning takes place, preferably in the ortho- or para-position to the electrophilic substituents. The said reaction takes place in a solvent at a temperature below 50°C, in particular at −40° to +30°, in the presence of silver ions. Solvents used are non-nucleophilic solvents, especially halogenated or nitrated aliphatic hydrocarbons, such as methylene chloride or 1,2-dichloroethane or nitromethane, or aromatic solvents, for example halogenated or nitrated solvents, such as benzene or nitrobenzene, or sulphur dioxide. The silver ions in particular originate from salts whereof the anion is weakly nucleophilic, such as silver perchlorate, silver chloroborate, silver trinitrobenzenesulphonate or above all silver tetrafluoborate.

The said reaction is advantageously carried out using 1 to 2 mol equivalents of the α-halogenonitrone and a corresponding amount of the silver salt per equivalent of aromatic compound. If more α-halogeno-nitrone is used, it is possible to introduce the acetaldo-nitrone radical several-fold, for example twice, into the aromatic structures.

If an aromatic group which is separated from the nitrone group by at least 3 carbon atoms is present in the starting substance, this reaction can also take place intramolecularly.

To isolate the nitrone it is possible to shake the reaction mixture, if appropriate after filtering off silver halide produced, with an alkali metal cyanide or alkaline earth metal cyanide, such as sodium cyanide or potassium cyanide, for a short time, by which means by-products can easily be removed.

Aromatic compounds which are employed for the reaction mentioned are also to be understood to include heterocyclic aromatic compounds. In particular, compounds which can be subjected to a Friedel Crafts reaction can be employed. In particular there should be mentioned thiophene, furane or pyrrole compounds, for example thiophene, furane, benzofurane, N-lower alkyl- or N-lower acyl-, such as N-methyl-, N-ethyl- or N-acetyl-pyrroles or -benzopyrroles, toluene, cresol, dimethoxybenzene, dimethylbenzene, acetylaniline, indane, naphthalene and its lower alkyl, lower alkoxy or acylamino derivatives, phenanthrene or oestrone. The term "lower" is applied to radicals which contain 1–6 carbon atoms.

The N-substituted araliphatic nitrones which are obtained are largely new compounds which, used as intermediate products, undergo saponification to the corresponding aldehydes in the usual manner, for example with weak acids, and if a hydroxyl group is present in the ortho-position to the radical introduced, cyclisation with elimination of water can also occur. This makes it possible in a simple manner to add an oxomethylene radical on to an aromatic bond.

The aldehydes thus obtained may further be converted by methods known per se, e.g. oxydation into the corresponding alcohols or carboxylic acids.

The examples which follow explain the invention without however restricting it in any way.

EXAMPLE 1

2.3 g of N-cyclohexylhydroxylamine are added over the course of 2 hours at 0°C to a magnetically stirred solution of 1.95 g of freshly distilled α-chloropropanol in 100 ml of ether. After one hour, 50 ml of ether are added and after a further 2 hours a further 50 ml of ether and 100 ml of methylene chloride are added. The mixture is stirred at 0°C for a further hour, anhydrous magnesium sulphate is added and the mixture is dried at 0°C for 15 hours. The magnesium sulphate is filtered off and the solvent is evaporated on a rotary evaporator in an ice bath. The crude product is dissolved in 10 ml of ether in a water bath at 45°C, 25 ml of n-pentane are added, the mixture is left to stand for 2 hours at 0°C and the crystals produced are filtered off. The filter residue is rinsed with 10 ml of n-pentane. The resulting α-chloropropionaldo-N-cyclohexyl-nitrone melts, with decomposition, at 73°–75°C.

A further quantity is obtained from the mother liquor by evaporation on a rotary evaporator in an ice bath, dissolving the residue in 2.5 ml of ether, adding 10 ml of pentane and leaving the mixture to stand for 1.5 hours at −22°C and then additionally at 0°C.

The α-chloronitrone obtained turns yellow after 2 days at room temperature. After a further 2 days it becomes a brown oil. However, it is stable for several months at −22°C.

EXAMPLE 2

1.825 g of t-butyl-hydroxylamine in 50 ml of absolute ether are added to 1.858 g of chloroacetaldehyde-hemihydrate, dissolved in 50 ml of absolute ether, under argon at 0°C over the course of one hour, whilst stirring, in a 250 ml three-necked flask. The temperature is allowed to rise to room temperature and the mixture is stirred for a further 4 hours. The solution is dried over sodium sulphate and filtered under argon. After removing the ether in a water pump vacuum in the cold, the colourless residue is dissolved in 50 ml of absolute methylene chloride and the solution is left to stand in an oil bath for 30 minutes. The chloroacetaldehyde-t-butylnitrone thus obtained can be kept at approx. −20°C in this solution if air is excluded, but cannot be kept as the substance itself. (NMR: 1.50/s(9H), 4.36/d J=5.5 H₂(CH₂ Cl),

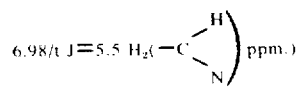

EXAMPLE 3

A solution of 0.20 g of N-cyclohexyl-acetaldonitrone in 4 ml of absolute carbon tetrachloride is dripped slowly into a suspension of 0.19 g of N-chlorosuccinimide in 5 ml of absolute carbon tetrachloride at 0°C (under nitrogen and with exclusion of light) whilst stirring. After stirring for three hours the succinimide which floats to the top is filtered off at 0°C under nitrogen. This filtrate is employed directly for the next reaction stage. The chloronitrone obtained is extremely labile but can be converted by means of a solution of 2,4-dinitrophenylhydrazine in methanol containing hydrochloric acid into the 2,4-dinitrophenylhydrazone of monochloroacetaldehyde of melting point 157°C.

For crystallisation, the filtrate obtained is evaporated in the cold. The residue is suspended in a little ether. On adding pentane, crystallisation commences. The mixture is left to stand in an ice bath for 2 hours and the product is filtered off. α-Chloro-acetaldo-N-cyclohexyl-nitrone, thus obtained, decomposes at 70°–75°C, giving a brown colouration.

If instead of N-chlorosuccinimide a corresponding amount of N-bromosuccinimide is taken and the procedure described above is followed, the extremely unstable α-bromoacetaldo-N-cyclohexyl-nitrone is obtained.

EXAMPLE 4

8.864 g of solid chloroacetaldehyde hemihydrate are dissolved in 250 ml of ether and 11.516 g of N-cyclohexylhydroxylamine are added in small portions over the course of one hour whilst cooling externally with an ice bath and stirring vigorously. Hereupon, a colourless precipitate separates out. A further 250 ml of ether are added and the mixture is stirred for 5 hours at 0°C, in the course of which the precipitate dissolves. The solution is dried for 2 hours at 0°C over sodium sulphate, whilst stirring, and is left to stand overnight at −20°C with exclusion of moisture. After slowly thawing out to room temperature, the sodium sulphate is filtered off using a glass frit and is washed three times with ether. The ether is stripped off on a rotary evaporator in a waterpump vacuum through a potassium hydroxide tower. Thereafter the mixture is cooled in an ice bath, whereupon a colourless solid residue is produced.

This residue is crystallised by suspending it in 250 ml of ether and warming the suspension on a water bath whilst swirling it vigorously. 200 ml of pentane are added to the resulting yellow solution, whereupon a crystallisation commences immediately. The mixture is left to stand, well-sealed, in an ice bath for 2 hours, a further 100 ml of pentane are added and the mixture is cooled in an ice bath for a further 2 hours. After slowly warming to room temperature, the crystals are filtered off and last remnants of ether are pumped off in a high vacuum using 2 cold traps and cooling with an ice bath. α-Chloro-acetaldo-N-cyclohexylnitrone is thus obtained in the form of colourless crystals which decompose at 72°–75°C with a brown colouration.

The substance can be kept for a fairly long time at −20°C. At room temperature, it assumes a yellow colour, and resinifies, after a few hours.

By concentrating the mother liquors it is possible to obtain a crystalline residue which after recrystallisation from 50 ml of ether and 50 ml of pentane gives yet a further portion of the nitrone described.

EXAMPLE 5

20 ml of sulphur dioxide are condensed at −40°C in a mixture of 138 mg of 1,4-dimethoxybenzene and 392 mg of silver tetrafluoborate, 378 mg of α-chloropropionaldo-N-cyclohexylnitrone in 1.5 ml of 1,2-dichloroethane are added dropwise at −20°C over the course of one hour, the reaction mixture is left to stand for half an hour at approx. −10°C under a reflux condenser, 20 ml of 1,2-dichloroethane are added and the sulphur dioxide is flushed out with nitrogen. The resulting solution is rapidly filtered through Cellite in 12 ml of a 15% strength aqueous potassium cyanide solution and the Cellite is rinsed with 30 ml of methylene chloride. The reaction solution is shaken for 1 minute in a separating funnel, both phases are filtered through Cellite and the Cellite is rinsed with 20 ml of methylene chloride. The phases are then separated, the aqueous phase is washed with 20 ml of methylene chloride and the combined organic phases with 10 ml of a saturated sodium chloride solution, and the organic phases are dried over sodium sulphate. The resulting crude product is adsorbed on 20 g of aluminium oxide (activity V, basic). On elution with benzene-ether (3:1) 240 mg of the crystalline nitrone of the formula

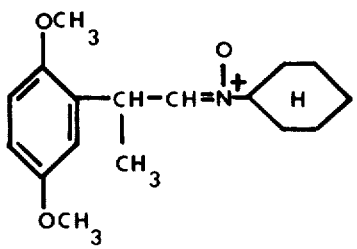

are obtained, which melts at 107°C after recrystallisation from pentane-hexane.

100 mg of this nitrone are dissolved in 50 ml of methylene chloride and the solution is stirred for 30 minutes at approx. 0°C with 10 ml of a 5% strength aqueous hydrochloric acid solution. After the usual working up and distillation of the product, 39 mg (= 60% of theory) of α-methyl-α-(2,5-dimethoxy-phenyl)-acetaldehyde are obtained. [Boiling point approx. 110°C at 0.05 mm Hg, IR: 1,730 cm$^{-1}$ (CO band)].

On starting from a corresponding amount of 1,4-dimethylbenzene and in other respects following the procedure described above, the N-cyclohexylnitrone of the α-methyl-α-(2,5-dimethyl-phenyl)-acetaldehyde of melting point 150°C (yield 40% of theory) and α-methyl-α-(2,5-dimethyl-phenyl)-acetaldehyde [boiling point 110°C/0.05 mm Hg; IR: 1,730 cm$^{-1}$ (CO band)], in approx. 60% yield, are obtained.

EXAMPLE 6

A solution of 0.625 g of α-chloro-propionaldo-N-cyclohexyl-nitrone in 10 ml of dry dichloromethane is added dropwise, whilst stirring, to a solution, cooled to −10°C, of 0.644 g of silver tetrafluoborate in about 25 ml of sulphur dioxde and of 0.128 g of naphthalene in 7 ml of dry dichloromethane, the mixture is stirred for a further 5 hours at −10°C, the solvent is then evaporated off under a water-pump vacuum whilst twice adding 10 ml of dry dichloromethane, and the residue is taken up in dichloromethane. This solution is shaken for 2 minutes with a solution of 3 g of potassium cyanide in 20 ml of water, the organic layer is separated off and the aqueous phase is extracted 4 times with dichloromethane. The combined organic solutions are twice washed with a saturated sodium chloride solution, the wash solutions are extracted once with dichloromethane, and the organic solutions are combined, dried and evaporated. The residue is adsorbed on 40 g of neutral aluminium oxide and eluted with hexane, then with a benzene-hexane mixture (1:5) and then with ether-benzene (1:20). The hexane eluate gives a little unreacted naphthalene and the benzene-hexane mixture gives a nitrile which after recrystallisation from cold (−20°C) pentane melts at 138°C. This proved to be 2-cyclohexyl-3-cyano-4-methyl-3,4,4a,10 a-tetrahydro-2H-naphtho[1,2-e]-1,2-oxazine. The ether-benzene eluate gives N-cyclohexyl-α-naphthyl-(1)-propionaldo-nitrone, which was recrystallised from hot hexane.

If this nitrone is reacted with a 5% strength aqueous hydrochloric acid solution, α-naphthyl-(1)-propionaldehyde is obtained, which distils at 170°–171°C at 14 mm Hg.

EXAMPLE 7

A solution of 243 g of N-cyclohexyl-α-chloro-δ-phenylvaleraldehydo-nitrone, obtained from δ-phenylvaleraldehyde by chlorination with sulphuryl chloride and reaction of the resulting chloroaldehyde with N-cyclohexylhydroxylamine, in 45 ml of dry dichloroethane, is added dropwise over the course of 1½ hours, whilst stirring, to a solution of 164 mg of silver tetrafluoborate in 50 ml of dichloroethane at −25°C. The cooling bath is removed and the reaction mixture is allowed to warm to room temperature over the course of 10 minutes and is then shaken with a solution of 0.5 g of potassium cyanide in 20 ml of water, and the aqueous layer is separated off. The latter is extracted 3 times with dichloromethane and the combined organic phases are twice washed with a saturated sodium chloride solution, the wash solution in each case being extracted with dichloromethane. The organic constituents are dried over magnesium sulphate and evaporated. The pale yellow residue is taken up in a little dichloromethane and the solution is filtered through 4 g of neutral aluminium oxide, the latter being rinsed with about 30 ml of dichloromethane, and is evaporated. The residue is dissolved in about 10 of hexane and the solution is filtered and evaporated. N-Cyclohexyl-naphthyl-(1)-acetaldo-nitrone of melting point 119°C is thus obtained. Chromatography of the residue on 6 g of neutral aluminium oxide and elution with ether-benzene (1:9) gives a further quantity of this nitrone.

EXAMPLE 8

432 mg of silver tetrafluoborate and 305 mg of hydroquinone dimethyl ether are first introduced into a flask fitted with a cold finger. After fitting a dropping funnel sealed by a serum cap and equipped with a pressure compensating device, the apparatus is evacuated 5 times under a waterpump vacuum and is subsequently filled with dry nitrogen. Sulphur dioxide was then condensed in the apparatus at −20°C until the volume of the solution is 40 ml. A solution of 2-chloropropanal-N-cyclohexylnitrone in 10 ml of absolute methylene chloride is then introduced into the dropping funnel and is added dropwise over the course of 2 hours to the vigorously stirred sulphur dioxide solution. The temperature is kept at −10°C for a further 6 hours and the sulphur dioxide is then pumped off in a waterpump vacuum. Towards the end, fresh methylene chloride is added in portions in order to keep the volume at between 10 and 20 ml. After filtering off the silver chloride (through Celite, with rinsing with 3×15 ml of methylene chloride), the filtrate is vigorously stirred with 60 ml of 5% strength hydrochloric acid for 5 hours and then separated off. After washing with concentrated sodium bicarbonate solution and concentrated sodium chloride solution (each wash solution being extracted with 2×10 ml of methylene chloride), and drying with sodium sulphate, the solution is evaporated and the yellow-brown oil which remains is filtered through 10 g of aluminium oxide IV (column filled with hexane and eluted with 30 ml of hexane and 80 ml of 4:1 hexane-benzene). The concentrated eluate is distilled in a rotating bulb tube at 90°C/2 mm Hg. α-(2,5-Dimethoxyphenyl)-propionaldehyde is thus obtained.

EXAMPLE 9

The following are initially introduced into a 50 ml two-necked flask under dry nitrogen: 5 ml of 1,2-dichloroethane, 808 mg of silver tetrafluoborate and 129 mg of p-cresol. After cooling to −20° C, 20 ml of sulphur dioxide are condensed in the apparatus, a solution of 783 mg of N-cyclohexyl-α-chloro-propionaldo-nitrone in 15 ml of 1,2-dichloroethane is introduced into the dropping funnel through the serum cap, and this solution is introduced dropwise into the flask over the course of 1½ hours whilst stirring well. The mixture is stirred for a further 8 hours at −20° C, the sulphur dioxide is then evaporated off in a waterpump vacuum at about 0° C and the silver chloride is filtered off. The filtrate is concentrated to approx. 5 ml on a rotary evaporator at about 40° C and is added dropwise over the course of one minute to 50 g of 40% strength oxalic acid which is vigorously boiling and evolving steam. After about 300 ml of distillate have been collected, the latter is saturated with sodium chloride and extracted 4 times with 40 ml of methylene chloride at a time. The solution is dried and concentrated on a rotary evaporator at 40° C. The residue is distilled at 11 mm Hg. α-[3,5-Dimethylbenzofuranyl-(7)]-propionaldehyde thus obtained, passes over at about 130° C.

EXAMPLE 10

5 ml of 1,2-dichloroethane (absolute), 215 mg of silver tetrafluoborate and 108 mg of p-cresol are initially introduced under dry nitrogen into a 50 ml two-necked flask equipped with a cold finger and dropping funnel (pressure-compensating device and serum cap). After cooling to −20° C, 20 ml of dry sulphur dioxide are condensed in the apparatus. A solution of 208 mg of N-cyclohexyl-α-chloro-propionaldo-nitrone in 15 ml of 1,2-dichloroethane is introduced into the dropping funnel through the serum cap and this solution is introduced dropwise into the flask over the course of 1 hour with vigorous stirring. The mixture is stirred for a further 8 hours at −20° C, the sulphur dioxide is then completely stripped off in a waterpump vacuum, the silver chloride is filtered off through Cellite and the filtrate is evaporated to 5 ml on a rotary evaporator at 40° C. The resulting concentrate is added dropwise over the course of one minute to 50 g of 40% strength oxalic acid which is vigorously boiling and evolving steam. After 250 ml of water have been distilled off, the distillate is saturated with sodium chloride and extracted 3 times with 40 ml of methylene chloride at a time and the combined organic phases are washed twice with 10 ml of 5% strength sodium hydroxide solution at a time, dried over sodium sulphate and evaporated on a rotary evaporator at 40° C in a waterpump vacuum. The colourless residue is distilled in a rotating bulb tube at 11 mm Hg. The colourless oil which passes over at 90° C is 3,5-dimethyl-benzofurane.

If N-acetyl-aniline is reacted analogously, 3-methyl-N-acetyl-indole of melting point 65° C (from dilute ethanol) is obtained.

If benzofurane is used as the starting material and the procedure described above is followed, α-[benzofuranyl-(2)]-N-cyclohexyl-propionaldonitrone is obtained prior to saponification, and this can be saponified to give α-(benzofuranyl-[2])-propionaldehyde.

EXAMPLE 11

10 ml of 1,2-dichlorroethane (absolute), 7,236 g of silver tetrafluoborate and 1,34 g of isobutyl-benzene are initially introduced under dry nitrogen into a two-necked flask equipped with a cold finger and dropping funnel (pressure-compensating device and serum cap). After cooling to −22° C, about 150 ml of dry sulphur dioxide are condensed in the apparatus. The third of a solution of 7.01 g of N-cyclohexyl-α-chloro-propionaldo-nitrone in 36 ml of 1,2-dichloroethane is introduced into the dropping funnel through the serum cap and this solution is introduced dropwise into the flask over the course of 3 hours with vigorous stirring. The mixture is stirred for a further 9 hours at −22° C. The other two positions are added in the same way each time 9 hours after last addition and again after 9 hours the sulphur dioxide is then completely stripped off in a waterpump vacuum. The yellow mixture is then filtered off through Cellite and washed well with methylene chlorids. The filtrate is evaporated to 40 ml. The resulting concentrate is added dropwise over the course of 20 minutes to 80 g of oxalic acid in 250 ml of water which is vigorously boiling and evolving steam. After 500 ml of water have been distilled off, the distillate is extracted 5 times with 60 ml of methylene chloride at a time and the combined organic phases are dried over sodium sulphate and evaporated on a rotary evaporator at 40° C in a waterpump vacuum.

The residue, about 2 g of a yellow oil, is adsobed on 55 g of aluminium oxide (activity V, neutral). The column is first eluted with about 50 ml hexane, then with 10 ml of a mixture of hexane and benzeme (1:1) and again with 20 ml of the hexane-benzene (1:1) mixture. The hexane fraction was discareded, the hexane-benzene fractions distilled separatly at about 85°C/0,004 Torr. The first hexane-benzene fraction yielded 101 mg of a colorless oil consisting of about 60% of α-(p-isobutylphenyl)-propionaldehyde and about 40% of α-(o-isobutylphenyl)-propionaldehyde. The second hexane-benzene fraction yield 307 mg of pure α-(p-isobutylphenyl)-propionaldehyde.

190 mg of α-(p-isobutylphenyl)-propionaldehyd are dissolved in 15 ml of acetone, and the solution cooled to −25° C is added to 220 ml of a solution containing 30 g chromiumtrioxide, 25 ml of concentrated sulfuric acid and water per 100 ml. The whole stirred for one hour at −25° C, the temperature was allowed to rise to about 0° C while stirring and then the reaction mixture was poured into a mixture of 20 ml water and 60 ml of methylene chloride. The two phases are separated and the watery phase washed two times with 30 ml of methylene chloride each time. The organic layers are dryed over magnesiumsulfat and evaporated. These were obtained 157 mg of α-(p-isobutylphenyl)-propionic acid, which melted after recrystallisation from few hexane at 74°-75.5°. This compound is known as "IBUPROFEN" and is used as antiinflammatory agent (cf. Brit. Pat. No. 971,700 and French Pat. No. 1,545,270).

What we claim is:

1. A process for preparing nitrones of the general formula

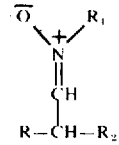

wherein R represents a member selected from the group of thiophenyl, furyl, benzofuryl, N-lower alkyl- or N-lower alkanoyl-pyrryl or -benzopyrryl, toluyl, cresyl, dimethoxyphenyl, dimethylphenyl, acetylaminophenyl, indanyl, naphthyl and its lower alkyl, lower alkoxy or lower alkanoylamino derivatives, phenanthryl and oestronyl, $R_1$ denotes 5 or 6 ringmembered cycloalkyl or lower alkyl and $R_2$ denotes hydrogen or lower alkyl, phenyl or phenyl-lower alkyl, which comprises reacting the compounds of the formulae R—H and

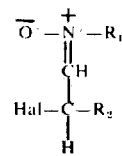

wherein Hal represents chloro or bromo and $R_1$ and $R_2$ have the abovementioned meaning, in the presence of silver ions and a solvent at a temperature below 50° C.

2. Process according to claim 1, wherein the silver ions used are ions of salts of which the anions are weakly nucleophilic.

3. Process according to claim 1, wherein the silver ions are derived from silver tetrafluoborate.

4. Process according to claim 1, wherein sulphur dioxide or nitromethane or a halogenated lower hydrocarbon is used as the solvent.

* * * * *